US008034973B2

(12) United States Patent
Goncalvez De Almeida et al.

(10) Patent No.: US 8,034,973 B2
(45) Date of Patent: Oct. 11, 2011

(54) PROCESS FOR OBTAINING HIGHLY SOLUBLE LINEAR ALKYLBENZENE SULFONATES (75) Inventors: José Luis Goncalvez De Almeida, Algeciras (BR); José Luis Berna Tejero, Boadilla del Monte (ES)

(73) Assignee: Cepsa Quimica, S.A., Madrid (ES)

( * ) Notice: Subject to any disclaimer, the term of this patent is extended or adjusted under 35 U.S.C. 154(b) by 310 days.

(21) Appl. No.: 12/293,256

(22) PCT Filed: Mar. 16, 2006

(86) PCT No.: PCT/ES2006/000131
§ 371 (c)(1),
(2), (4) Date: Jul. 1, 2009

(87) PCT Pub. No.: WO2007/104805
PCT Pub. Date: Sep. 20, 2007

(65) Prior Publication Data
US 2009/0299091 A1 Dec. 3, 2009

(51) Int. Cl.
*C07C 309/31* (2006.01)
(52) U.S. Cl. ............... 562/94; 562/93; 562/95; 562/96; 562/97
(58) Field of Classification Search ............ 562/93, 562/94, 95, 96, 97
See application file for complete search history.

(56) References Cited

U.S. PATENT DOCUMENTS

| 5,157,158 | A | 10/1992 | Berna Tejero et al. |
| 5,276,231 | A | 1/1994 | Kocal et al. |
| 6,133,492 | A | 10/2000 | Anantaneni |
| 6,521,804 | B1 | 2/2003 | Marinangeli et al. |
| 6,562,776 | B1 | 5/2003 | Smith et al. |
| 2003/0166481 | A1 | 9/2003 | Smith et al. |

FOREIGN PATENT DOCUMENTS

| WO | WO 00/40551 | 7/2000 |
| WO | WO 01/68517 | 9/2001 |
| WO | WO 2006/108883 | 10/2006 |

OTHER PUBLICATIONS

Almeida et al. "Linear Alkylbenzene." *Journal of the American Oil Chemists' Society*, vol. 71, No. 7. 1994. pp. 675-694.
Cavalli et al. "Iso-Branching of Linear Alkylbenzene Sulphonate (LAS). Biodegradable Study of Two Model Compounds." *Toxicological and Environmental Chemistry*, vol. 54. 1996. pp. 167-186.
Falbe. "Surfactants in Consumer Products: Theory, Technology and Application."1987. pp. 3-7.
Goncalves de Almeida. "Alkylation of Benzene by 1-Dodecene on Zeolite Catalysts." Unpublished doctoral dissertation presented at the Claude Bernard University—Lyon I, Villeurbanne, France. 1994. pp. 1-4; R-178; 71-73.
Meier et al. "Atlas of Zeolite Structure Types." *Zeolites 17:A1-A6*. 1996. pp. A3-A5; 12; 104-105; 152-153.
Nielsen et al. "Environmental Fate of Commercial LAS: An Overview on the Fate of the Iso-Branched and Dialkyltetralin Co-Products.".
Satterfield. "Heterogeneous Catalysis in Industrial Practice" *Second Edition*. 1980. pp. 209-213.
Shah. "UOP HF Alkylation Process."
Venuto et al. "Organic Reactions Catalyzed by Crystalline Aluminosilicates." *Journal of Catalysis*, vol. 5. 1965. pp. 81-98.
Zinner et al. "Catalytic activity of lanthanide-doped Y zeolite on the alkylation of benzene with 1-dodecene model reaction." *Journal of Alloys and Compounds*, 193. 1993. pp. 65-67.
Deshmukh et al. "Alkylation of benzene with long chain (C8-C18) linear primary alcohols over seolite-Y." *Catalysis Letters*. vol. 64. 2000. pp. 247-250.
Sivasanker et al. "Distribution of Isomers in the Alkylations of Benzene with Long-Chain Olefins over Solid Acid Catalysts." *Journal of Catalysis*. vol. 138. 1992. pp.
Thomas et al. "Towards a Green Synthesis of LAB's: Effect of Rare Earth Metal Ions on the Benzene Alkylation with 1-Dodecene over NaFAU-Y Zeolites." *J. Mater.Sci.* vol. 41. 2006. pp. 1611-1616.

*Primary Examiner* — Peter O Sullivan
(74) *Attorney, Agent, or Firm* — Merchant & Gould, P.C.

(57) ABSTRACT

The present invention relates to a process for obtaining a highly soluble linear alkylbenzene sulfonate with an adjustable 2-phenyl isomer content and an extremely low sulfonation color, in which a catalytic system based on highly stable solid catalysts and with a high selectivity for linear monoalkylated compounds is used.

24 Claims, 4 Drawing Sheets

PROCESS FOR OBTAINING HIGHLY SOLUBLE LINEAR ALKYLBENZENE SULFONATES

This application is a National Stage Application of PCT/ES2006/000131, filed 16 Mar. 2006, and which application is incorporated herein by reference and a claim of priority is made.

FIELD OF THE INVENTION

The present invention generally relates to catalytic alkylation reactions and particularly to zeolite type catalysts.

STATE OF THE ART

Alkyl aromatic compounds are an important family of substances that are used as raw materials in many industrial fields, such as the field of plasticizers, polymeric materials, insecticides, in agriculture for preventing the agglomeration of fertilizers, in the manufacture of textiles and fabrics, in the leather and fur industry, herbicides, industrial cleaning processes, in the photography industry, in the manufacture of adhesives and in fire-fighting products such as wetting agents, in electrochemical processes for removing dirt and grease from the surface of a substrate, and in biodegradable detergents (Surfactants in Consumers Products, Theory, technology and Application, edited by J. Falbe, Springer Verlag, 1987).

The usual process used by the petrochemical industry to produce alkyl aromatic compounds, especially for applications in detergents, consists of dehydrogenating linear paraffins to obtain linear mono-olefins and then carry out the alkylation of benzene with said mono-olefins. Linear alkylbenzene sulfonate (LAS) is produced by the sulfonation of linear alkylbenzene (LAB) and subsequent neutralization of the corresponding sulfonic acids (HLAS). The linear olefins used in this process have between nine and sixteen carbon atoms. The alkylation step occurs in liquid phase, on the presence of Friedel-Craft type catalysts, for example, hydrofluoric acid. The HF process is well known and commercially used, producing a high yield (>99% by weight) in LAB with a relatively low selectivity for the 2-phenyl isomer, lower than 20%. The integrated process for the production of LAB is described in the Handbook of Petroleum Refining Process, published by Robert A. Meyers, 1986, p. 1-23, incorporated herein as a reference. U.S. Pat. No. 5,276,231 describes the intermediate steps of the process for the production of LAB, such as the selective hydrogenation of the diolefin by-products formed in the dehydrogenation of paraffins and the removal of non-linear by-products from the stream of the dehydrogenation step. The use of HF has some drawbacks, because it requires careful handling and special equipment due to its corrosivity, which translates into an increase of the fixed and operating costs, therefore the development of alternative catalysts based on solids with an acid character has been attempted.

The prior art reports the use of many solid acid catalysts for the production of phenyl alkanes, such as synthetic faujasites (zeolites X and Y), zeolite L, ZSM-5, ZSM-18, ZSM-20, mordenite and offretite. Recent developments which have used several types of zeolites, amorphous silica-alumina and other types of materials as alkylation catalysts are described for the production of LAB with a 2-phenyl isomer content in the range of 20% to 80% by weight (J. L. Berna Tejero, A. Moreno Danvila U.S. Pat. No. 5,157,158, 1992; and J. L. G. De Almeida, M. Dufaux, Y. Ben Taarit and C. Naccache, Journal of the American Oil Chemist's Society, Vol. 71, no. 7, 675-694,1 1994). The zeolite solids mentioned herein as catalysts are defined in the classification of the Atlas of Zeolite Framework Types, W. M. Meier, D. H. Olson -and C. H. Baerlocher, 5th revised edition, 2001, Elsevier, to which the present invention refers.

One of the crystalline aluminosilicates that could be used as a catalyst in this type of reactions is a type of zeolite of the FAU family denominated zeolite Y, the composition of which is the following:

$$Na_{56}[Al_{56}Si_{136}O_{384}]:250H_2O$$

Zeolite Y has a porous, three-dimensional structure with the pores arranged perpendicularly to one another in the x, y and z planes. The pore diameter is large, about 7.4 Å, given that the aperture is defined by a 12-member oxygen ring, and leads into a large cavity of diameter 12.5 Å. It structurally comprises a three-dimensional network of $SiO_2$ and $AlO_4$ tetrahedrons joined to one another through common oxygen atoms. When the tetravalent silicon ion is substituted isomorphically with a trivalent aluminium atom in a silicon network comprising silicon tetrahedrons, the resulting net negative charge must be stabilized by a nearby positive ion, such as a proton. The latter can be produced by water dissociation, forming a hydroxy group on the aluminium atom. The resulting structure is a Brönsted acid (C. N. Satterfield, Heterogeneous Catalysts in Practice, McGraw-Hill Inc. 1980, page 152). If the latter is heated, the water of constitution is extracted and the Brönsted acid sites are converted into Lewis acid sites. Dehydrated zeolites can exhibit both Brönsted and Lewis acid sites, depending on the Ion exchange and heat treatment conditions. As a result of their microporous structure, zeolites can generate a much greater number of accessible acids sites per surface area of the solid than in the standard catalyst based on amorphous silica-alumina used in alkylation.

In practice, when the aromatic compound is alkylated using solid acid catalysts, dialkylated as well as monoalkylated products are formed, especially when the reaction takes place in high conversion conditions and the aromatic compound is benzene. Apart from the acidity, zeolite Y has another important property related to catalytic activity. Due to their crystalline structure, zeolitic channels or pores are microscopically small, therefore their reduced dimensions and their molecular architecture have extraordinary effects on the selectivity of a reaction because they can prevent the formation of more voluminous compounds such as some types of heavy alkylates, also known as dialkylbenzenes. This effect is denominated size exclusion selectivity.

It is well known that the presence of rare earth elements can strongly affects the strength and density of the acid sites in the zeolitic material. (L. B. Zinner, K. Zinner, M. Ishige and A. S. Araujo, Catalytic activity of lanthanide-doped Y zeolite on the alkylation of benzene with 1-dodecene model reaction, Journal of Alloys and Compunds, 193, 65-67, 1993). The aluminosilicate exchanged with rare earth elements is an activated crystalline catalyst in which the nuclear structure has been modified because it has chemisorbed or ionically bonded rare earth metal cations. Rare earth cations can be provided starting from the salt of a single metal or preferably from a mixture of salts of different metals such as light rare earth chlorides or didymium chlorides (La, Ce, Pr, Nd, CAS: 11098-090-1). In most applications, rare earth mixtures are preferred because they can be easily obtained commercially and are much more cost-effective than purified rare earth metals. P. B. Venua et al published in the Journal of Catalysts, 4, 81-98, 1966, the potential use of highly acid solid catalysts such as faujasites of the zeolite X and Y type with ion exchange with rare earth metals, denominated REY and REX, for the alkylation of benzene with olefins. A Brazilian patent, P.I. no. 9204326-7 of Deten Quimica S. A. shows the use of a catalyst based on a zeolitic faujasite, specifically zeolite Y, activated with Ca and lanthanides, specifically La, Ce, Nd or Gd. The patent claims a process in a solid-liquid batch reactor operating in complete mixture conditions, with a superacid catalyst, operating at temperatures as low as 80° C.

Another alkylation catalyst that is frequently used in these reactions is a zeolite with a MOR type structure, a mordenite, which is characterized by a $SiO_2/Al_2O_3$ molar ratio of 10. Its typical cell composition unit is:

$$Na_8[(AlO_2)_8(SiO_2)_{40}] \cdot 24H_2O$$

The crystalline structure shows a system of channels of 12-member rings with a free diameter of 6.7×7 Å, and these main channels are interconnected by small side channels circumscribed by 8-member rings with an aperture of 2.9×5.7 Å. These small channels prevent the passage of most organic molecules; as a result, the porous network of mordenite is basically seen as a one-way pore structure. The process for dealuminizing mordenite by hydrotreatment followed by treatment with acid can modify its structure and catalytic characteristics, increasing the adsorption capacity and the diffusion rate of the molecules as commented in the reference entitled "Alquilation du benzène par le 1-dodecene sur catalyseurs zeolithiques", J. L. Almeida, PhD, thesis presented in Université Claude Bernard-Lyon 1, 1994. The following patents, US patent no. 2003/0166481-A1, U.S. Pat. No. 6,521,804-B1, U.S. Pat. No. 6,133,492 and U.S. Pat. No. 6,562,776-B1, incorporated herein as a reference, describe alkylation processes wherein the mordenite type catalyst can be mixed with different catalysts which do not produce a high 2-phenyl isomer content, therefore the amounts of each catalyst must then be adjusted to provide the desired levels of 2-phenyl isomer in the product.

The process producing alkyl aromatics or alkylates by means of the alkylation of benzene with long chain olefins is characterized, in terms of selectivity, by the heavy alkylate content, the 2-phenyl isomer content and also by the branched alkylate content. These chemical species determining the effectiveness of the process and the quality of the product depend mainly on the type of catalyst, on the quality of the starting material and on the operative conditions of the process.

The heavy alkylate group comprises the total of the chemical species with molecular weights exceeding that of the monoalkylated product. They are generally formed by dialkylbenzenes, diphenylalkanes, oligomerized olefins and alkylates of these oligomerized olefins formed during the alkylation step. These products are mainly generated by the alkylation of a monoalkylbenzene previously formed with an olefin. Diphenyl alkanes are formed by the alkylation of benzene with a diolefin which has been dehydrocyclized. The formation of this type of products is not desired because it decreases the general yield of the process and can degrade the quality of the quality of the produced alkylate, thus reducing its economic viability. There are additionally other compounds to be considered, for example, some alkyl polyaromatic products, generated by the alkylation with monoolefins of polyaromatic compounds generated in the dehydrogenation step. These products can be eluted together with the heaviest LAB compounds, because their distillation temperature range overlaps with that of said LAB. These products drastically decrease the quality of the sulfonated end product, HLAS, because its sulfonation color increases very much.

The 2-phenyl isomers are those alkylated molecules having the aromatic ring joined to the alkyl chain in position 2 of the chain. The 2-phenyl isomer content is defined as the percentage by weight of the 2-phenyl isomer in a LAB or LAS mixture, and is it calculated by the following formula:

2-phenyl isomer[%]=(weight of 2-phenyl isomer)*100/(total weight of LAB or LAS)

The LAB mixtures with a content of external isomers (2+3 phenyl) exceeding 60% by weight are characterized by providing a LAS with an improved surface activity after sulfonation and neutralization. These LAS, however, show an important drawback caused by their low solubility in cold water, low stability in high viscosity conditions. LAS mixtures comprising more than 60% by weight of external isomers (2+3 phenyl) tend to form highly insoluble and highly viscous gels, making them difficult to handle and process. This is the reason for which it would be desirable to incorporate a hydrotrope, for the purpose of improving the solubility of the final surfactant when the 2-phenyl isomer content is greater than 60% by weight. Although there are many patents relating to the use of hydrotropes, one of them is considered to be the most recommendable for this process. PCT/ES2005000169 relates to a process for obtaining a suitable hydrotrope starting from previously dehydrogenated paraffins, specifically starting from those by-products extracted during the monoolefin purification step.

Finally branched alkylates can be defined as the percentage of the total monoalkylate where the alkyl chain bonding with the aromatic ring is not a linear or normal alkyl group but a branched one. These non-normal alkyl groups have radicals such as methyl, ethyl, propyl, isopropyl, butyl, isobutyl, tert-butyl, and diverse variants of hexyl, heptyl, octyl bonded in any place of the alkyl chain except in the ends of the chain. Branched alkylates are generated by the alkylation of those branched paraffins present in the fresh starting paraffins, or by alkyl transposition processes occurring during the dehydrogenation and alkylation steps. Branched alkylates include alkylates having one of the carbon atoms of the aliphatic alkyl group in a quaternary carbon position. The quaternary carbon atom in the alkyl chain is defined as a carbon joined to four other carbon atoms and one of these can be bonded to a carbon atom of the phenyl group, forming a quaternary alkyl phenylalkane. If the quaternary carbon is the second carbon atom of the alkyl chain, the quaternary carbon present in the resulting 2-alkyl-2-phenylalkane can be called "terminal quaternary carbon". It is known that this species, like simple branched alkylates, has a biodegradation rate similar to that of linear alkylbenzene sulfonate. However, when the quaternary carbon is any other carbon atom of the alkyl chain, for example 5-metyl-5phenylalkane, it is called "internal quaternary carbon", and the corresponding alkylbenzene sulfonate has a much slower biodegradation rate. The articles entitled "Iso-branching of LAS biodegradation study of two model compounds", L. Cavalli, G. Cassani, M. Lazzarin, C. Maraschin, G. Nuzzi, J. L. Berna, J. Bravo, J. Ferrer, A. Masno, Toxicology & Environmental Chemistry. Vol. 54, page 167-186, 1966 and "Biodegradation of co-products of commercial LAS", A. M. Nielsen, L. N. Britton, L. Cavalli, J. L. Berna, The Cler 20 Review, Vo 1.2, No. 1, page 14-27, 1996, provide scientific proof of the biodegradation behavior of these alkylbenzene derivatives.

The alkylation reaction can finally be evaluated with the following indices: conversion, selectivity for the monoalkylbenzene, distribution of isomers and deactivation rate:

i) alkylation conversion or, more specifically, fractional conversion: in the alkylation reaction considered in this invention, benzene is always used in stoichiometric excess with respect to the olefins. Fractional conversion can be defined as the fraction of the limiting reactant, in this case, the olefin, which is consumed to generate all the products, thus:

$$\text{Conversion} = \frac{N_{A0} - N_A}{N_{A0}} * 100$$

wherein $N_{AO}$ is the number of moles of olefin at the reactor inlet and $N_A$ is the number of moles of the same reactant at the reactor outlet.

ii) Selectivity for monoalkylbenzene: it is defined as

$$Sel_{monoalkylbenzene} = \frac{W_{monoalkylbenzene}}{W_{light} + W_{monoalkylbenzene} + W_{heavy\,alkylate}} * 100$$

wherein $W_{monoalkyalte}$ s the weight of the produced monoalkylbenzene of interest, $W_{light}$ is the weight of all the by-products lighter than the lightest monoalkylbenzene of interest, and $W_{heavy\,alkylate}$ is the total weight of all those species, the molecular weights of which are greater than those of the produced monoalkylates, and as has been indicated, are generally formed by dialkylbenzenes, diphenylalkanes, oligomerized olefins and alkylates of these oligomerized olefins. The weights or weight percentages of each family of products can be used to calculate the selectivity.

iii) Distribution of isomers: Among the produced monoalkylbenzenes the distribution of isomers can be defined as the percentage by weight of each type of isomer produced, such as 2-phenyl, 3-phenyl . . . 6-phenyl isomers, and also the branched alkylate.

linear 2-phenyl isomer (R = linear)

linear 3-phenyl isomer (R = linear)

linear 6-phenyl isomer (R = linear)

branched n-phenyl isomer
(branched R and/or R', n = 2-6)

The distribution of isomers has an important role in the overall economic feasibility of the production process, in the quality of the end sulfonated product and also in its biodegradation rate.

iv) Catalyst deactivation rate: this variable is defined as the ratio between the activity of the catalyst at a considered time and the activity of the catalyst at time zero:

Catalyst deactivation rate=activity of the catalyst (t)/activity of the catalyst (t=0)

The activity of the catalyst is considered in terms of conversion:

Catalyst deactivation rate=conversion (t)/conversion (t=0)

The deactivation of the catalyst is due to either the poisoning of the active centers (irreversible deactivation) and/or to contamination processes (formation due to collision on active centers or pores of the catalyst, generally reversible by means of controlled combustion or pyrolysis).

There is therefore a need to find a process for obtaining a very soluble linear alkylbenzene sulfonate with maximized detersive properties, an extremely low sulfonation color, an optimal environmental behavior and in maximum effectiveness conditions for the use of raw materials.

DESCRIPTION OF THE INVENTION

The present invention relates to a very efficient process for obtaining a highly soluble linear alkylbenzene sulfonate with an adjustable 2-phenyl isomer content and an extremely low sulfonation color, wherein a catalytic system is used that is based on highly stable solid catalysts and with a high selectivity for linear monoalkylated compounds, such that the problems described in the state of the art are solved.

Therefore, a first aspect of the invention relates to a process for obtaining a highly soluble linear alkylbenzene sulfonate with a 2-phenyl isomer content between 18% and 70% by weight, by means of the catalytic alkylation of an aromatic compound with an alkylating agent comprising the following steps:

i) catalytically dehydrogenating a linear paraffin feed, linear mono-olefins, unconverted paraffins and a certain amount of by-products such as diolefins and non-linear compounds being obtained.

ii) selectively hydrogenating the diolefins produced as a by-product in step i) to mono-olefins, a raw alkylating agent thus being obtained.

iii) purifying the raw alkylating agent by separating the non-linear products contained in the effluent of step ii), a purified alkylating agent formed by mono-olefins and paraffins thus being obtained.

iv) treating the non-linear products extracted in step iii) to form the hydrotropic precursor.

v) alkylating the aromatic hydrocarbon with the mono-olefins present in the purified alkylating agent, by means of the combination of two alkylation processes based on:
  a) an alkylation process with a catalyst producing a raw linear alkyl aromatic compound with a maximum 2-phenyl isomer content of 20% by weight
  b) an alkylation process with a catalyst producing a raw linear alkyl aromatic compound with a minimum 2-phenyl isomer content of 20% by weight vi) fractioning the effluent of step v) for the purpose of separating the aromatic compounds which have not reacted, the paraffins and the heaviest by-products of the alkyl aromatic compounds of interest vii) purifying the fraction of alkyl aromatics of interest coming from step vi)

viii) sulfonating the purified linear alkyl aromatics obtained in step vii)

ix) neutralizing the linear alkyl sulfonic acid produced in step viii)

This process is characterized in that the catalyst producing a maximum of 20% of 2-phenyl isomer comprises a FAU type zeolite, between 0.01%-0.15% by weight of at least one of the metals selected from the group consisting of: Li, Na, K, Mg or Ca and between 0.1%-8.0% by weight of at least one of the rare earth metals selected from the group consisting of La, Ce, Pr, Nd, Pm, Sm or Eu; and in that the catalyst producing a minimum of 20% of 2-phenyl isomer comprises a MOR type zeolite, between 0.01%-0.20% by weight of at least one of the metals selected from the group consisting of: Li, Na, K, Mg or Ca, a maximum of 0.01% of Na and between 0-0.5% by weight of at least one of the metals selected from the group consisting of Ti, Zr, Hf, Ti.

In the present invention, FAU type or EMT-FAU type zeolites refer to the group of zeolites with isotypic structures corresponding to the FAU structure type, such as: zeolite Y, zeolite Na—X, siliceous zeolite Na—Y, zeolite linde X, zeolite linde Y, zeolite ZSM-3 and zeolite ZSM-20, preferably a zeolite Linde Y or a zeolite Y.

In the present invention, MOR type zeolites refer to the group of zeolites with isotypic structures corresponding to the MOR structure type, such as: mordenite, zeolite Na—D and zeolite Ca—Q, more preferably to mordenite.

In a particular embodiment, the catalyst producing a maximum of 20% by weight of 2-phenyl isomer comprises:
a) a zeolite with a FAU type isotopic structure, preferably a zeolite Y
b) between 0.01-0.15% by weight of at least one of the metals selected from the group consisting of: Li, Na, K, Mg or Ca, preferably about 0.08% by weight of Na.
c) between 0.1-8% by weight of at least one of the rare earth metals selected from the group consisting of La, Ce, Pr, Nd, Pm, Sm or Eu, preferably between 3-4% by weight of La, between 0.5-1.5% by weight of Ce, between 0.1-1% by weight of Pr and between 1-2% by weight of Nd.

In a particular embodiment, the catalyst producing a maximum of 20% by weight of 2-phenyl isomer is structurally and texturally characterized by:
a) an X-ray powder diffraction pattern characterized in that the most intense peak appears at a 2 theta angle corresponding to 6.2°, and the remaining main peaks appear at 2 theta diffraction angles corresponding to 23.6°, 27°, 31.3°, 15.6°, 20.3°, 18.6°and 30°, ordered from greater to lesser intensity of the associated peaks.
b) a total silicon/aluminium molar ratio between 1:1 and 3:1, preferably 1.6:1.0.
c) a total specific area (BET) comprised between 400-700 $m^2/g$, preferably 650 $m^2/g$
d) a micropore area comprised between 350-600 $m^2/g$, preferably 525 $m^2/g$.
e) a specific micropore volume comprised between 0.1-0.3 ml/g, preferably 0.21 ml/g
f) a macropore distribution wherein the macropore diameter is in the range comprised between 20-2000 angstroms, preferably between 20 and 80 angstroms.

In a particular embodiment, the catalyst producing a minimum of 20% by weight of 2-phenyl isomer comprises:
a) a zeolite with MOR type isotypic structure
b) between 0.01%-0.2% by weight of at least one of the metals selected from the group consisting of: Li, Na, K, Mg or Ca, preferably 0.07% by weight of Mg
c) a maximum of 0.01% of Na
d) between 0-0.5% by weight of at least one of the metals selected from the group consisting of Ti, Zr, Hf, Ti, preferably 0.25% by weight of Ti.

In a particular embodiment, the catalyst producing a minimum of 20% by weight of 2-phenyl isomer is structurally and texturally characterized by:
a) an X-ray powder diffraction pattern characterized in that the most intense peak appears at a 2 theta angle corresponding to 25.6° and the remaining main peaks appear at 2 theta diffraction angles corresponding to 22.30, 26.3°, 19.6°, 13.5°, and 27.7° ordered from greater to lesser intensity of the associated peaks.
b) a total silicon/aluminium molar ratio between 1.5:1.0-3.5:1.0, preferably 2.8:1.0
c) a total specific area (BET) comprised between 150-600 $m^2/g$, preferably 490 $m^2/g$.
d) a specific micropore area comprised between 300-450 $m^2/g$, preferably 380 $m^2/g$.
e) a specific micropore volume comprised between 0.01-0.2 ml/g, preferably 0.15 ml/g.
f) a macropore distribution wherein the macropore diameter is in the range comprised between 20-800 angstroms, preferably between 20 and 300 angstroms.

In a particular embodiment of the present invention, the paraffins of step i) comprise straight chain alkanes comprising between 8-30 carbon atoms, preferably between 10-16 carbon atoms, more preferably between 10-14 carbon atoms. These paraffins can be dehydrogenated and purified by means of any process described in the state of the art.

In a particular embodiment of the present invention, the aromatic hydrocarbon is the aromatic hydrocarbon selected from the group: toluene, xylene, benzene or mixtures thereof, it is preferably benzene.

In a particular embodiment of the present invention, the aromatic compound and the olefins are mixed before the alkylation reaction of step v) in a benzene:olefin molar ratio comprised between 5:1-70:1, preferably between 10:1-30:1, more preferably between 10:1-15:1. in a particular embodiment, it further comprises between 0-0.3% by weight of non-linear compounds. In a particular embodiment, it further comprises between 0-0.1% by weight of water.

In a particular embodiment of the present invention, the alkylation reaction of step v) is carried out in a reactor with a catalyst arrangement selected from the group consisting of: a fixed catalytic bed with a single catalyst, at least one fixed catalytic bed with two completely mixed different solid catalysts, at least two differentiated fixed catalytic beds, each one with the same catalyst, at least two differentiated fixed catalytic beds, each one with different catalysts, and a fluidized bed reactor with one or more different catalysts.

In a particular embodiment, the alkylation reactions are carried out simultaneously in a reactor configuration comprising at least one of the reactor configurations selected from the group of: an independent reactor, at least two parallel reactors, at least two reactors in series and combinations thereof.

In a particular embodiment, the purification process of step iii) is carried out by means of purification techniques known by a person skilled in the art such as for example, hydrogenation, fractioning and selective adsorption. In the case of a selective adsorption, the adsorbing bed is formed by at least one of the materials selected from the group consisting of: zeolites, silica, silica gel, macroporous magnesium silicate, activated alumina, silica-alumina, clays, molecular sieves, cellulose acetate, macroporous polystyrene gel, activated carbon and organoselective polymeric membranes.

In a particular embodiment, the purification process of step iv) is carried out by means of purification techniques known by a person skilled in the art such as for example, hydrogenation, fractioning and selective adsorption. In the case of a selective adsorption, the adsorbing bed is formed by at least one of the materials selected from the group consisting of: zeolites, silica, silica gel, macroporous magnesium silicate, activated alumina, silica-alumina, clays, molecular sieves, cellulose acetate, macroporous polystyrene gel, activated carbon and organoselective polymeric membranes.

In a particular embodiment, the purification process of step vii) is carried out by means of purification techniques known by a person skilled in the art such as for example, hydrogenation, fractioning and selective adsorption. In a preferred embodiment, the purification process of step is carried out by means of selective adsorption by means of a clay type selective adsorbent comprising:

a) a total silica-alumina molar ratio between 3:1 and 6:1, preferably between 3.5:1.0 and 5.5:1.0, more preferably 4.2:1
b) between 1%-4% by weight of Fe, preferably 2.1% by weight
c) between 0.5%-2% by weight of K, preferably 1.2% by weight
d) between 0.2%-2% by weight of Mg, preferably 0.7% by weight
e) between 0.1-1.0% by weight of $TiO_2$, preferably 0.3% by weight
f) a total specific area, expressed as BET area, comprised between 150-500 $m^2/g$, preferably between 200400 $m^2/g$, more preferably 260 $m^2/g$;
g) an accumulative pore volume between 0.1-2.0 ml/g, preferably 0.4 m/g;
h) a macropore distribution wherein the macropore diameter is comprised between 20-800 angstroms, preferably between 20-200 angstroms, more preferably between 20-100 angstroms, with an average diameter in terms of a pore volume centered in 34 angstroms.

In a particular embodiment, the hydrotropic precursor of step iv) is added to the alkyl aromatic stream before the purification of step vii), the purification, sulfonation and/or neutralization, being thus jointly purified and sulfonated.

In a particular embodiment, the hydrotropic precursor of step iv) is purified, sulfonated and/or neutralized and subsequently added to the alkyl aromatic sulfonate obtained after step viii).

In a particular embodiment the neutralization process of step ix) is carried out by means of an alkaline substance comprising one or more cations selected from the group: Na, K, $NH^{4+}$, Mg, Ca, Ba or by means of substituted ammonium alkalis.

In a particular embodiment, the temperature of the reaction is comprised between 20-400° C.

In a particular embodiment, the space velocity is comprised between 1 $h^{-1}$ and 15 $h^{-1}$.

Another aspect of the present invention relates to a process for obtaining a highly soluble linear alkylbenzene sulfonate with a 2-phenyl isomer content of at least 18% by weight by means of the catalytic alkylation of an aromatic compound with an alkylating agent as described previously, wherein steps i), ii), iii) and iv) are optional.

In a more particular embodiment, the olefins are α-olefins, and comprise between 18-28 carbon atoms, preferably between 20-24 carbon atoms, and can additionally include a maximum of 10% by weight of branched olefins.

In a more particular embodiment of the present invention, the aromatic compound and the α-olefins are mixed before the alkylation reaction of step v) in an aromatic:olefin molar ratio comprised between 5:1-70:1.

In a more particular embodiment, it further comprises between 0-0.1% by weight of water.

Another aspect of the present invention relates to suitable cleaning compositions for preparations for washing dishes, cleaners for hard surfaces, liquid washing products, powdered washing products, cleaning preparations in the form of pastes, gels, washing bars, comprising:

a) between 1-99% by weight of a soluble linear alkylbenzene sulfonate obtained by means of a process according to any of the previous considerations
b) between 99-1% by weight of other detergent ingredients selected from the group formed by fatty alcohol derivatives, co-surfactants, structurers, solvents, additives and mixtures thereof, such as fatty alcohol derivatives, fatty acids, alkyl sulfates, an ethanolamine, an amine oxide, alkaline carbonates, ethanol, isopropanol, water, pine oil, sodium chloride, sodium silicate, polymers, alcohol alcoxylates, perborate salts, zeolites, alkaline sulfates, enzymes, hydrotropes, colorings, fragrances, preservatives, brighteners, incorporators, polyacrylates, essential oils, alkaline hydroxides, ether sulfonates, water-soluble branched alkylbenzene sulfonates, alkyl phenol alcoxylates, fatty acid amines, alpha-olefin sulfonates, paraffin sulfonates, betaines, chelating agents, tallowamine ethoxylates, polyether amine ethoxylates, ethylene oxide/propylene oxide block copolymers, low-foam alcohol surfactants of ethylene oxide/propylene oxide, methyl ester sulfonates, alkyl polysaccharides, n-methyl glucamides, sulfonated alkyl diphenyl oxide and polyethyelene glycol.

DETAILED DESCRIPTION OF AN EMBODIMENT

Figure 1:
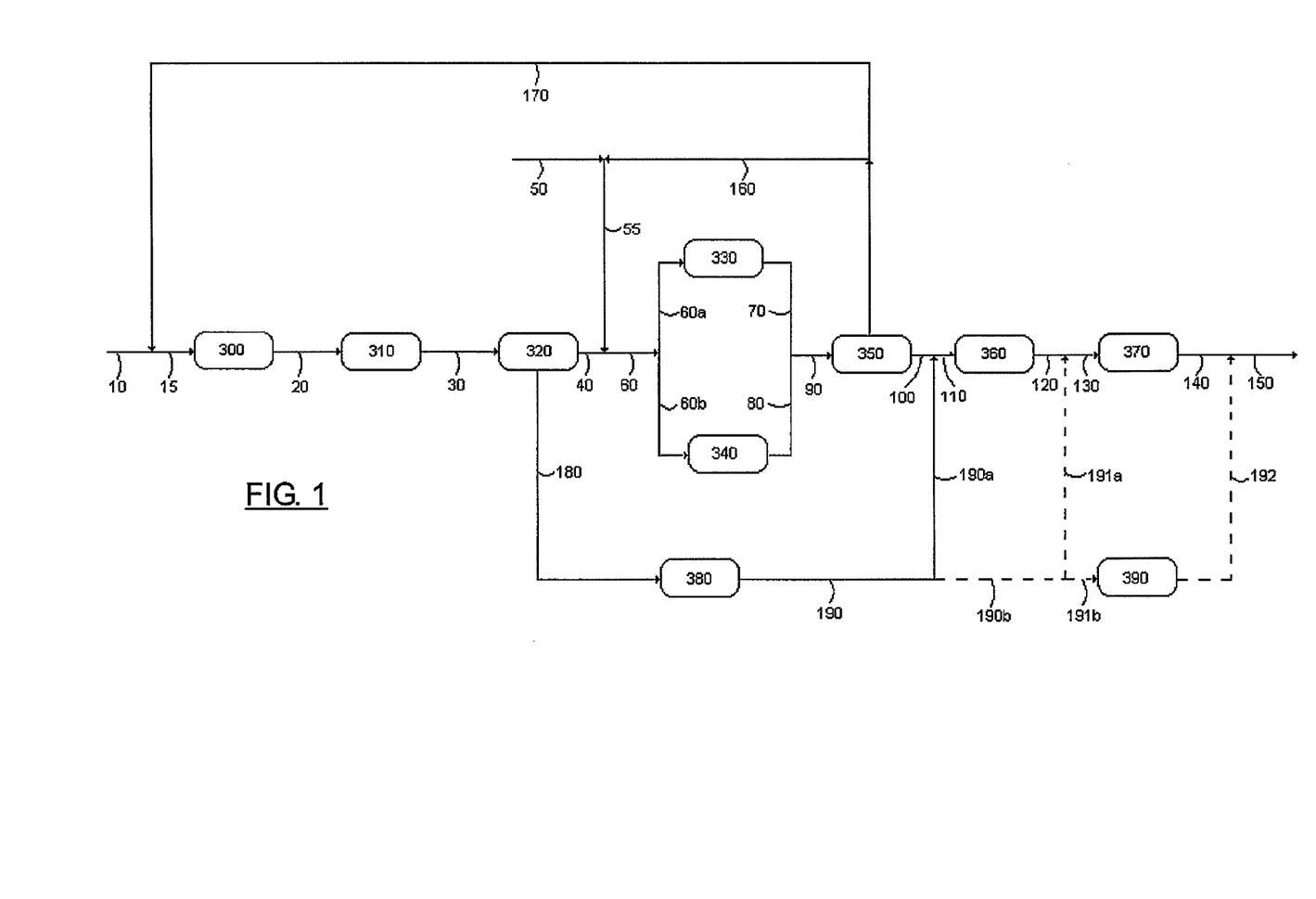
FIG. 1 shows a scheme of the reaction of the present invention in the form of a flow diagram.

FIG. 1 shows a non-limiting scheme for putting this invention into practice.

Stream 15 is the paraffin feed to the dehydrogenation unit, and comprises the fresh paraffin mixture, stream 10, with the unconverted paraffins separated in the raw alkylbenzene purification unit, unit 350, and recycled through stream 170. The dehydrogenation unit 300 partially converts the paraffin feed into a mixture of mono-olefins, paraffins and diverse by-products such as diolefins and non-linear compounds. The olefin purification unit, unit 310, is fed with the effluent of the dehydrogenation unit through stream 20, increasing the net yield of mono-olefins upon converting some of the by-products generated in the dehydrogenation unit, mainly diolefins, into mono-olefins. The resulting stream, stream 30, is processed in unit 320 containing a selective adsorbent for eliminating the non-linear compounds produced in the dehydrogenation process. Fresh benzene is pumped into the process through stream 50 and is mixed with recycled benzene which has not reacted (stream 160) coming from the raw alkylbenzene purification unit, unit 350. The mixture of these two streams forms the benzene feed (steam 55), which is mixed with the effluent (stream 40) of the selective adsorption unit 320 to form stream 60, formed by mono-olefins, benzene and paraffins and fed to the alkylation units.

Stream 60 is divided into two identical streams, 60a and 60b, feeding two different alkylation reactors, units 330 and 340 respectively; the alkylation reactor 330 uses a catalyst producing a raw linear alkylbenzene (stream 70) with a maximum 2-phenyl isomer content of at least 20% by weight, whereas the alkylation reactor 340 Uses a catalyst producing a raw linear alkylbenzene (stream 80) with a 2-phenyl isomer content of at least 20% by weight. Streams 70 and 80 are mixed in different proportions to generate a stream, stream 90, containing linear alkylbenzene with a variable 2-phenyl isomer content, unreacted benzene, paraffins and by-products. Stream 90 is fed to the raw alkylbenzene purification unit, unit 350, wherein the unreacted benzene, the paraffins and the by-products heavier than the linear alkylbenzene are distilled for the purpose of obtaining a relatively pure linear alkylbenzene (stream 100). Afterwards, stream 100 is fed to the final alkylbenzene purification step, unit 360, which contains a selective adsorbent for eliminating aromatic compounds which are still present in small amounts in the relatively pure alkylbenzene due to the fact that the distillation temperature range overlaps with that of the alkylbenzene of interest.

The non-linear compounds extracted in unit 320 are pumped to the specific treatment unit 380 through stream 180. This unit 380 comprises steps such as fractioning, hydrogenation and/or selective adsorption to transform the non-linear impurities in the hydrotropic precursor (stream 190). Depending on the operating conditions of the process of this invention, stream 190 can be led through streams 190a or 190b, or it cannot be used if the 2-phenyl isomer content of the linear alkylbenzene is less than 60% by weight. The relatively pure linear alkylbenzene stream, stream 100, and the hydrotropic precursor stream 190a can thus be mixed forming stream 110, they are purified together in unit 360 and are then sent through streams 120 and 130 to unit 370, where they are sulfonated/neutralized together, generating the final stream, stream 150. Stream 190a can also be omitted, such that the relatively pure linear alkylbenzene coming from unit 350, stream 100-110, is separately purified in unit 360, and once it is purified (stream 120) is then mixed with the hydrotropic precursor provided by streams 190b and 191a, generating stream 130, being thus sulfonated and neutralized together in unit 370, thus generating the final stream, stream 150. Streams 190a and 191a can also be omitted, such that the relatively pure alkylbenzene of stream 100 is purified (unit 360), sulfonated and neutralized (unit 370) alone, separately generating the alkylbenzene sulfonate stream. This stream 140 is then mixed with stream 192, corresponding to the hydrotrope that is separately sulfonated and neutralized in unit 390 through streams 190, 190b and 191b, thus generating the final stream 150. The stream 150 comprises a highly soluble linear alkylbenzene sulfonate with a controlled 2-phenyl isomer content and a low sulfonation color. The addition of the hydrotrope (in any of its variants) is carried out when the 2-phenyl isomer content exceeds 60% by weight.

Figure 2:
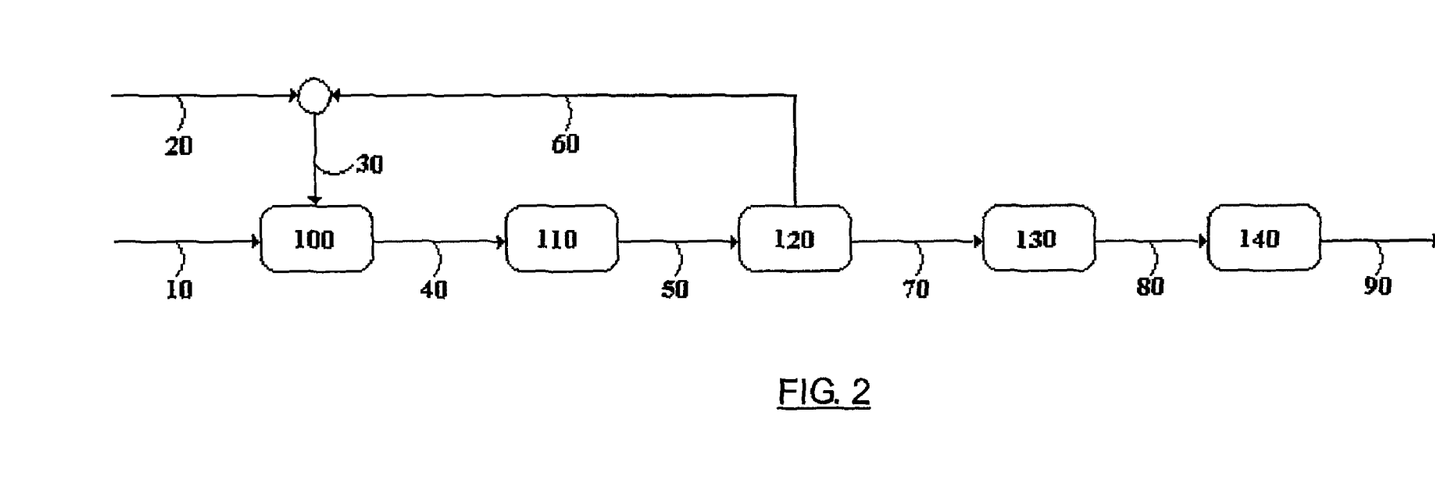
FIG. 2 shows a scheme of the reaction of the present invention in the form of a flow diagram when the steps of catalytic paraffin dehydrogenation, diolefin hydrogenation, purification of the alkylating agent and purification and addition of the hydrotropic precursor are omitted.

FIG. 2 shows another non-limiting scheme for putting this invention into practice, when steps i), ii), iii), and iv) are optional.

Stream 10 is the fresh alpha-olefin feed to the process. Stream 20 is the fresh feed of aromatic compound, such as benzene, to the process. Stream 20 is mixed with stream 60, which forms the recycle of the aromatic compound excess once it has been separated from the alkylation process in a distillation column, unit 120. Stream 30, which is the aromatic compound feed, is generated by mixing streams 20 and 60. This stream 30 is mixed with stream 10 in the mixing unit 100, for the purpose of obtaining a mixture of the aromatic compound and the olefins with the desired aromatic-olefin molar ratio, stream 40. This stream is fed to the alkylation reactor, unit 110, where the catalyst is placed in a fixed-bed reactor, such that the alkylation of the aromatic compound is produced by the olefins. The effluent of the alkylation reaction, stream 50, is formed by the unreacted aromatic compound and the alkyl aromatic compound generated during the alkylation. Stream 50 is separated in a distillation column, unit 120, for the purpose of separating the aromatic compound which has not reacted at its upper part, stream 60, and the alkyl aromatic compound at its lower part, stream 70. Stream 60 is re-circulated to the process, as mentioned previously, whereas stream 70 is sulfonated in a falling-film reactor with gaseous $SO_3$, unit 130. The sulfonated product, stream 80, is formed by highly pure, linear alkyl aromatic sulfonic acid, with a certain 2-phenyl isomer content. This product can then be neutralized in unit 140 with basic calcium, barium, sodium, magnesium and ammonium salts, in the presence of a highly ionizable compound, such as phenol, for the purpose of obtaining a highly pure alkyl aromatic sulfonate, both neutral and preferably overbased depending on the amount of base used in the neutralization.

The invention is additionally described, for illustrative purposes only, through the following examples which must not be considered as limiting the scope of the present invention.

EXAMPLES

Example 1

This example shows the advantages of using a Y zeolyte doped with 7% by weight of rare earth metals such as La, Ce, Pr and Nd (called catalyst A) in the alkylation of benzene with a mixture of olefins/paraffins, in comparison with the use of a commercial amorphous fluorinated silica-alumina (called catalyst B), widely used in this reaction at an industrial scale. Both catalysts were ground and sieved to obtain an equivalent particle size distribution. The benzene was dried with a molecular sieve to minimize the addition of water, and it was then mixed with a mixture of mono-olefins and paraffins that came from the dehydrogenation of paraffins and the selective hydrogenation of diolefins. The pilot plant alkylation tests were carried out in an isothermal fixed-bed reactor, with 24-hour reaction cycles followed by catalyst regeneration cycles by washing with benzene for the same time period. A standard cycle comprises a 24-hour reaction cycle at 140° C., LHSV=11 h$^{-1}$ and a benzene:olefin molar ratio of 30:1, followed by a washing cycle with benzene for the same time period. The catalyst weight, the washing conditions, etc., are summarized in Table 1:

TABLE 1

| Catalyst | A | B |
|---|---|---|
| Particle diameter (mm) | 0.50-1.25 | 0.50-1.25 |
| Catalyst volume (cm$^3$) | 122 | 122 |
| Reaction temperature (° C.) | 100-150 | 115-170 |
| Regeneration temperature (° C.) | 260 | 260 |
| Reaction pressure (kgf/cm$^2$) | 20 | 20 |
| Regeneration pressure (kgf/cm$^2$) | 40 | 40 |
| Reaction LHSV (h$^{-1}$) | 4-11 | 2-4-11 |
| Regeneration LHSV (h$^{-1}$) | 1 | 1 |
| Benzene/olefin molar ratio | 10-30 | 10-30 |

The composition of the starting raw material, referring to the mixture of olefins and paraffins, is summarized in Table 2:

TABLE 2

| Compound | Percentage (% by weight in the mixture) |
|---|---|
| n-C10 | 14.8 |
| n-C11 | 31.0 |
| n-C12 | 26.1 |
| n-C13 | 18.2 |
| n-C14 | <0.9 |
| C10-olefin | 1.3 |
| C11-olefin | 3.2 |
| C12-olefin | 3.1 |
| C13-olefin | 2.3 |
| C14-olefin | <0.1 |
| Aromatic compounds | <0.1 |

This mixture of paraffins and olefins is mixed with dry benzene until the desired benzene:olefin molar ratio is achieved. The catalyst evaluations were carried out in five different sequences of reaction cycles. Once each reaction cycle was developed, the alkylation effluent was distilled in three steps using three distillation columns (the first one operating at atmospheric pressure whereas the other two operated under vacuum). The first column operated at atmospheric pressure, and separated the unreacted benzene at its head, whereas the compounds present at its bottom were fed into the second column. The second column separated paraffins at its head, whereas the compounds present at its bottom were fed into the third column. The third column separated the alkylbenzene at its upper part, and the heavy alkylate at its lower part. The analyses (carried out by GC-FID) refer to compounds fed to the third column. In the first sequence of reaction cycles, both catalysts were independently tested, using the same operating conditions. For each catalyst, the sequence comprised seven cycles, which were carried out with a LHSV of 11 h$^{-1}$ at temperatures of 130 and 140° C., followed by three cycles at 155° C. with a LHSV of 4 h$^{-1}$. Next, a standard cycle at 140° C. and a LHSV of 11 h$^{-1}$ was completed for the purpose of verifying the catalyst deactivation. In all of these cycles, the benzene to olefin molar ratio was kept at a value of 30. All the conditions and results are summarized in Table 3.

TABLE 3

| Cycle | Temperature (° C.) | LHSV (h$^{-1}$) | Conversion (% mol) | | Monoalkyl-benzene (% by weight) | | Branched alkylate (% by weight) | | Heavy alkylate (% by weight) | | 2-phenyl isomer (% by weight) | |
|---|---|---|---|---|---|---|---|---|---|---|---|---|
| | | | A | B | A | B | A | B | A | B | A | B |
| 1$^{st}$ | 140 | 11 | 100.0 | 92.9 | 98.4 | 95.9 | 6.5 | 3.1 | 0.6 | 3.3 | 18.7 | 29.5 |
| 2$^{nd}$ | 140 | 11 | 100.0 | 93.6 | 98.5 | 96.3 | 6.4 | 2.8 | 0.5 | 2.9 | 18.5 | 29.9 |
| 3$^{rd}$ | 140 | 11 | 100.0 | 93.9 | 98.8 | 96.5 | 6.3 | 2.9 | 0.3 | 2.8 | 18.5 | 29.8 |
| 4$^{th}$ | 130 | 11 | 99.9 | 76.0 | 98.4 | 96.9 | 5.7 | 0.9 | 0.7 | 2.4 | 18.4 | 30.8 |
| 5$^{th}$ | 130 | 11 | 99.9 | 75.8 | 98.4 | 96.0 | 6.0 | 1.1 | 0.7 | 3.3 | 18.3 | 30.7 |
| 6$^{th}$ | 130 | 11 | 99.9 | 76.8 | 98.5 | 96.4 | 5.8 | 1.8 | 0.6 | 3.0 | 18.4 | 30.5 |
| 7$^{th}$ | 140 | 11 | 100.0 | 94.3 | 98.5 | 95.5 | 6.9 | 3.1 | 0.5 | 3.8 | 18.4 | 29.6 |
| 8$^{th}$ | 115 | 4.0 | 100.0 | 89.5 | 98.3 | 96.2 | 5.1 | 0.9 | 0.8 | 3.3 | 18.5 | 30.6 |
| 9$^{th}$ | 115 | 4.0 | 100.0 | 89.9 | 98.3 | 95.8 | 5.2 | 0.9 | 0.8 | 3.6 | 18.4 | 30.6 |
| 10$^{th}$ | 115 | 4.0 | 100.0 | 90.0 | 98.4 | 96.5 | 5.2 | 0.9 | 0.8 | 2.9 | 18.4 | 30.6 |
| 11$^{th}$ | 140 | 11 | 100.0 | 95.6 | 98.4 | 94.7 | 6.8 | 2.4 | 0.6 | 4.6 | 18.4 | 29.9 |

In the second sequence of reaction cycles, the catalyst A was tested to analyze its activity at lower temperatures. This sequence comprised three reaction cycles which were carried out at a LHSV of 4 h$^{-1}$, but now at 100° C., followed by a standard cycle (LHSV =11 h$^{-1}$; T=140° C.). In all of these cycles, the benzene to olefin molar ratio was kept at a value of 30. All the conditions and results are summarized in Table 4.

TABLE 4

| Cycle/Catalyst | Temperature (° C.) | LHSV (h$^{-1}$) | Conversion | Monoalkyl-benzene (% bw) | Branched alkylate (% by weight) | Heavy alkylate (% by weight) | 2-phenyl isomer (% by weight) |
| --- | --- | --- | --- | --- | --- | --- | --- |
| 1$^{st}$/A | 100 | 4.0 | 99.8 | 98.2 | 3.8 | 1.1 | 18.2 |
| 2$^{nd}$/A | 100 | 4.0 | 99.9 | 98.4 | 3.8 | 0.9 | 18.2 |
| 3$^{rd}$/A | 100 | 4.0 | 99.8 | 98.5 | 4.0 | 0.8 | 18.2 |
| 4$^{th}$/A | 140 | 11.0 | 100.0 | 98.4 | 6.7 | 0.6 | 18.4 |

In the third sequence of reaction cycles, both catalysts were independently tested to analyze its deactivation rate. In order to force catalyst stability, after the standard cycle (LHSV =11 h$^{-1}$; T=140° C.), the normal reaction period of 24 hours was extended to 60 hours without the standard washing with benzene. In all of these cycles, the benzene to olefin molar ratio was kept at a value of 30. The catalyst activity was analyzed in terms of conversion. All the results and conditions are summarized in Table 5:

TABLE 5

| Hours of reaction | Temperature (° C.) | LHSV (h$^{-1}$) | Catalyst A conversion | Catalyst B conversion |
| --- | --- | --- | --- | --- |
| 24 | 140 | 11 | 100.0 | 93.9 |
| 30 | 140 | 11 | 100.0 | 93.1 |
| 36 | 140 | 11 | 100.0 | 92.2 |
| 42 | 140 | 11 | 99.9 | 91.1 |
| 48 | 140 | 11 | 99.9 | 89.7 |
| 54 | 140 | 11 | 99.5 | 88.5 |
| 60 | 140 | 11 | 98.9 | 85.6 |

The fourth sequence of reaction cycles, in which catalyst B was tested, comprised six reaction cycles which were carried out at a LHSV of 2 h$^{-1}$ (for the purpose of reaching a 100% conversion), at different temperatures, followed by a standard cycle (LHSV =11 h$^{-1}$; T=140° C.). In all of these tests, the benzene to olefin molar ratio was kept a value of 30. All these conditions and results are summarized in Table 6:

TABLE 6

| Cycle/Catalyst | Temperature (° C.) | LHSV (h$^{-1}$) | Conversion | Monoalkyl-benzene (% bw) | Branched alkylate (% by weight) | Heavy alkylate (% by weight) | 2-phenyl isomer (% by weight) |
| --- | --- | --- | --- | --- | --- | --- | --- |
| 1$^{st}$/B | 130 | 2.0 | 100.0 | 95.1 | 3.0 | 4.1 | 29.8 |
| 2$^{nd}$/B | 130 | 2.0 | 100.0 | 94.6 | 3.5 | 4.6 | 29.9 |
| 3$^{rd}$/B | 150 | 2.0 | 100.0 | 94.2 | 5.5 | 4.7 | 29.0 |
| 4$^{th}$/B | 150 | 2.0 | 100.0 | 94.4 | 5.7 | 4.6 | 29.2 |
| 1$^{st}$/B | 170 | 2.0 | 100.0 | 94.4 | 8.1 | 4.2 | 28.3 |
| 2$^{nd}$/B | 170 | 2.0 | 100.0 | 94.6 | 8.3 | 4.0 | 28.2 |
| 3$^{rd}$/B | 140 | 10.8 | 95.5 | 96.9 | 7.0 | 2.3 | 29.3 |

The fifth sequence of reaction cycles, in which only catalyst A was tested, comprised six reaction cycles; they were done with variable LHSV, temperatures and benzene to olefin molar ratio, for the purpose of analyzing the effect of the last variable on the conversion and selectivity of the reaction. All the conditions and results are summarized in Table 7:

TABLE 7

| Cycle/Catalyst | Temperature (° C.) | LHSV (h⁻¹) | Benzene/olefin molar ratio | Conversion | Monoalkyl-benzene (% by weight) | Branched alkylate (% by weight) | Heavy alkylate (% by weight) | 2-phenyl isomer (% by weight) |
|---|---|---|---|---|---|---|---|---|
| 1$^{st}$/A | 120 | 3.1 | 10 | 100.0 | 94.9 | 7.6 | 3.3 | 18.8 |
| 2$^{nd}$/A | 120 | 3.6 | 15 | 100.0 | 96.6 | 6.7 | 1.9 | 18.8 |
| 3$^{rd}$/A | 120 | 4.5 | 25 | 100.0 | 97.2 | 6.5 | 1.3 | 18.7 |
| 4$^{th}$/A | 120 | 4.9 | 30 | 100.0 | 98.0 | 5.9 | 0.7 | 19.1 |
| 1$^{st}$/A | 140 | 6.8 | 10 | 100.0 | 94.4 | 9.1 | 4.0 | 19.0 |
| 2$^{nd}$/A | 150 | 6.8 | 10 | 100.0 | 94.9 | 10.2 | 4.0 | 18.9 |

As can be seen in Table 3, the activity of catalyst A is much higher than that of catalyst B, because catalyst A reaches 100% conversion in almost all the cycles. Even when the temperature is 100° C. (LHSV=4h⁻¹, Table 4), approximately 100% conversion is reached with catalyst A, whereas catalyst B does not reach 100% conversion until very low space velocities and temperatures above 130° C. (Table 6). For the purpose of subjecting the catalyst activity to tension, the normal reaction period of 24 hours was extended to 60 hours in the third sequence (Table 5) and, in the case of catalyst A, even after the 50$^{th}$ hour of reaction, the observed conversion was greater than 99%, whereas with catalyst B deactivation was observed after 24 hours. This implies that catalyst A is much more stable against deactivation than catalyst B, therefore this catalyst allows operating in longer reaction cycles, reducing the number of washings with benzene during the life of the catalyst and, in conclusion, reducing the operating costs.

Another important advantage of catalyst A is associated with the production of heavy alkylate. As can be seen in Table 3, catalyst A produces a significantly lower amount of heavy subproducts than catalyst B (at least 80% less), reaching less than 1% of heavy alkylate in all those tests wherein the benzene to olefin molar ratio is 30:1.

FIG. 1 shows a GC-FID of the products generated in tests with a benzene to olefin molar ratio of 30 (once benzene and the paraffin are separated), corresponding to the products generated by catalyst A and catalyst B. Specifically, they correspond to the retention times of the heavy alkylate:

As can be seen in FIG. 1, catalyst A generates much less intense peaks in the chromatographic region corresponding to alkylbenzene-type compounds (heavy alkylates) than the amorphous catalyst B. These compounds have between 26 and 32 carbon atoms, and they are generated by the reaction of a monoalkylbenzene with an olefin, forming a dialkylbenzene compound (such as didecylbenzene, didocecylbenzene, decyldodecylbenzene, etc.). The advantage of using catalyst A is that its internal microporous structure involves size and shape restrictions minimizing the formation of these by-products, because its size is larger than the pore diameter of the catalyst.

For the purpose of analyzing the effect of the benzene to olefin molar ratio in the distribution of the product, the experiments summarized in Table 7 were carried out. As can be seen in Table 7, when this ratio decreases, the amount of heavy by-products increases, but even with the minimal molar ratio tested in this sequence (benzene to olefin molar ratio equal to 10, Table 7), when Table 7 is compared with Table 3, the amount of heavy by-products generated by catalyst A (approximately 3%) is less or equal to that generated by catalyst B in the highest molar ratio (benzene to olefin molar ratio equal to 30). Thus, catalyst A allows operating at a lower benzene to olefin molar ratio than catalyst B, which implies lower costs in the subsequent unreacted benzene separation step.

Finally, as can be seen in Table 3, catalyst A produces a relatively high amount of branched alkylate when compared to catalyst B. But catalyst A is more active than catalyst B, such that it is not necessary to operate the reaction system at temperatures as high as 130-140° C. (as can be observed in all the results, as the temperature increases, the branched content increases) to achieve 100% conversions. This means that when the reaction system is operated at an industrially reasonable space velocity (LHSV=4 h⁻¹) and keeping the temperature at 100° C. (Table 4), 100% conversion is achieved and the branched content in the alkylate decreases to 4% by weight, an acceptable value and similar to the one reached when catalyst B operates at 100% conversion (Table 6).

Example 2

This example shows the advantages of purifying the olefin/paraffin mixture coming from the dehydrogenation and selective hydrogenation steps, before it is reacted with benzene in the alkylation step. This reaction was catalyzed by a zeolite Y doped with a 7% (by weight) of rare earth metals such as La, Ce, Pr and Nd (called catalyst A). In this example, catalyst A is arranged on a fixed bed for the purpose of catalyzing the alkylation of benzene with purified and non-purified olefin/paraffin mixtures.

The purification step is carried out using an adsorbing bed, where a certain amount of a certain molecular sieve is placed. The selected molecular sieve is a zeolite, 13× widely used in processes for the selective elimination of aromatic components from a mixture of olefins and paraffins. The mixture of olefins and paraffins is passed through the bed to achieve a selective adsorption of non-linear compounds coming from the previous dehydrogenation step (or present in the fresh feed of paraffin and/or of the paraffin recycling). Once saturated, the bed is washed with short-chain paraffins to desorb the olefins and paraffins that could have been retained in the pores, and then they are moved with benzene, for the purpose of recovering the adsorbed aromatic compounds that can be used as hydrotropic precursors. The operating conditions for a purification step for a pilot plant are summarized in Table 8:

TABLE 8

| | |
|---|---|
| Size (standard US mesh) | 10 to 20 |
| Adsorption temperature (° C.) | 140 |
| Washing temperature (° C.) | 130 |
| Desorption temperature (° C.) | 140 |
| Adsorption pressure (kg/cm²) | 25 |
| Washing pressure (kg/cm²) | 25 |
| Desorption pressure (kg/cm²) | 25 |
| Washing agent | n-pentane |
| Desorption agent | benzene |
| LHSV (h⁻¹) | 2 |

The mixture of olefins and paraffins coming from the dehydrogenation and hydrogenation steps contained approximately 2% by weight of aromatic compounds. Its composition after the purification step is summarized in Table 9:

TABLE 9

| Compound | Percentage (% by weight in the mixture) |
|---|---|
| n-C10 | 14.8 |
| n-C11 | 31.0 |
| n-C12 | 26.1 |
| n-C13 | 18.2 |
| n-C14 | <0.9 |
| C10-olefin | 1.3 |
| C11-olefin | 3.2 |
| C12-olefin | 3.1 |
| C13-olefin | 2.3 |
| C14-olefin | <0.1 |
| Aromatic compounds | <0.1 |

Once purified, the mixture of olefins and paraffins was mixed with dry benzene to obtain the selected molar ratio. Then, this mixture was used as a feed in the alkylation step. The operating conditions for the alkylation step are summarized in Table 10. Other parameters associated with the fixed bed are the same as those summarized in Example 1 (catalyst A), because the alkylation with purified and non-purified mixtures is carried out in the same reactor and under the same conditions defined in this example. The distillation process carried out to separate the benzene, the paraffins, the alkylbenzenes and the heavy alkylate is as defined in Example 1. The GC analyses refers to the current fed to the third column. The light products are analyzed by GC-FID on the upper current of the first column.

TABLE 10

| Temperature (° C.) | 140 |
|---|---|
| Pressure (kg/cm$^2$) | 20 |
| LHSV (h$^{-1}$) | 11 |
| Benzene/olefin molar ratio | 30 |

Another test was carried out for the purpose of analyzing the effect of the purification step on the product distribution, keeping all operation variables at the same value as before but using a non-purified mixture. The product distribution referred to the alkylation with purified and non-purified mixtures is summarized in Table 11.

TABLE 11

| Product distribution | Purified mixture | Non-purified mixture |
|---|---|---|
| Alkylbenzene (% by weight) | 98.6 | 94.8 |
| Heavy alkylate % by weight) | 0.5 | 3.7 |
| Light (% by weight) | 0.9 | 1.6 |

Figure 3:
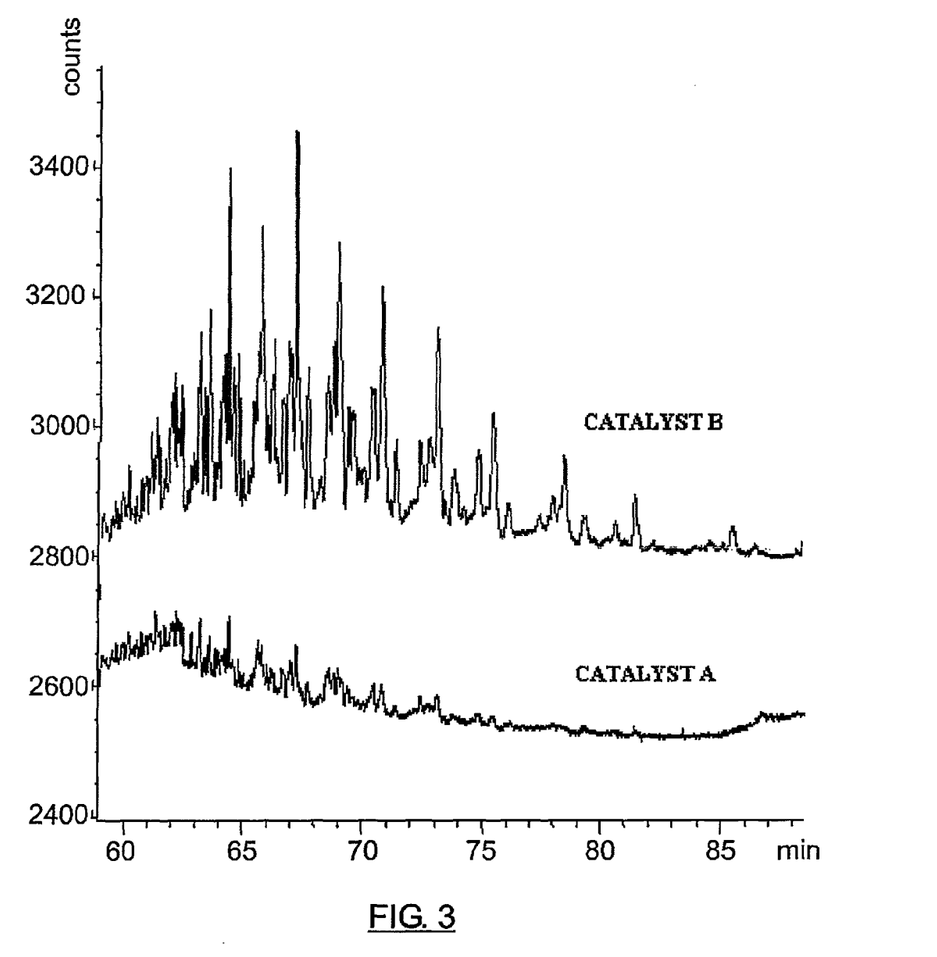
FIG. 3 simultaneously shows the two chromatograms generated by GC-FID of the obtained products, once the unreacted benzene and the paraffins have been separated, when the alkylation of benzene is carried out with a purified alkylating agent using two different catalysts separately: a catalyst used in a standard manner in similar alkylation processes (catalyst B) and one of the catalysts the use of which is claimed in this patent (catalyst A). The chromatogram specifically corresponds to the retention times of the heavy alkylate.
Figure 4:
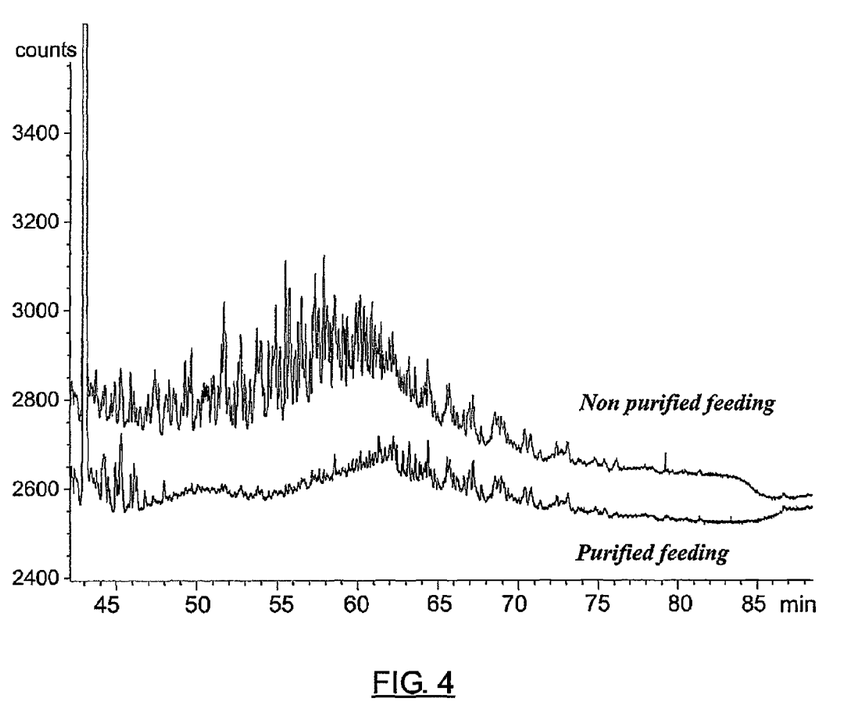
FIG. 4 simultaneously shows the two chromatograms generated by GC-FID of the obtained products, once the unreacted benzene and the paraffins have been separated, when the alkylation of benzene Is carried out with a purified alkylating agent and a non-purified alkylating agent, using one of the catalysts claimed in this patent.

As can been seen in Table 11, the amount of heavy alkylate generated when purified mixtures are used is reduced by 86% by weight in comparison to non-purified mixtures. FIG. 3 shows the chromatograms corresponding to the GC-FID of the obtained products, once the benzene and paraffins are separated, when the purified and non-purified mixtures are used:

The upper line corresponds to the use of a non-purified mixture, whereas the lower one corresponds to the use of a purified mixture. When comparing both chromatograms, it is clear that the lines of intensity of the peaks corresponding to the heavy alkylate produced by using purified mixtures is much lower than by using non-purified mixtures. The selective adsorption effect mainly affects the final content of the "lightest" heavy alkylate, located at retention times below 62 minutes as shown in FIG. 3. These products are mainly compounds of 20-22 carbon atoms, such as alkyl-fluorenes, alkyl-anthracenes, alkyl-phenanthrenes, indanes, indenes, etc. They are mainly generated by the alkylation of polyaromatic compounds, generated in the dehydrogenation step (such as anthracene, phenanthrene, fluorenes, etc.), with $C_{10}$-$C_{14}$ olefins. The purification of olefins and paraffins with an adsorbing bed involves the elimination of these products which are directly generated in the dehydrogenation step, or are contained in the fresh or recycle feed, and also the elimination of those polyaromatic compounds which can react with $C_{10}$-$C_{14}$ olefins in the alkylation step.

As can be seen in Table 11, the use of purified mixtures also involves a reduction in the final amount of light by-products. The amount of generated light by-products is reduced by 44% by weight when purified mixtures are used.

Example 3

This example shows the stability of zeolite Y doped with rare earth metals when it is used as a catalyst in the alkylation of benzene with olefins. A long sequence of cycles that use zeolite Y doped with rare earth metals has been carried out for the purpose of analyzing their deactivation rate. The thirty standard cycles were carried out, as previously defined in Example 1, at LHSV=8 h$^{-1}$ and T=140° C. After each 24-hour reaction cycle, a washing cycle was carried out for 24 hours. The results are summarized in Table 12 and they are an average of the cycles considered.

TABLE 12

| Cycles | Average conversion |
|---|---|
| 1$^{st}$ to 10$^{th}$ | 99.6 |
| 11$^{th}$ to 20$^{th}$ | 99.6 |
| 21$^{st}$ to 30$^{th}$ | 99.6 |

As can be seen in Table 12, throughout this sequence of reaction/regeneration cycles, the average conversion was always above 99.5%, and in the thirtieth cycle no deactivation with respect to the initial cycles was detected. This means that the zeolite Y doped with rare earth metals is a very stable catalyst, maintaining a high conversion over time and not showing any signs of deactivation.

Example 4

This example shows the advantages of using two parallel isothermal fixed-bed reactors, one of them loaded with the previously used zeolite Y doped with 7% (by weight) of rare earth metals such as La, Ce, Pr and Nd (called catalyst A) and the other one with a commercial crystalline mordenite, called catalyst C, adjusting the distribution of the previously purified feed between the two reactors and mixing the resulting effluents for the purpose of obtaining an adjustable 2-phenyl isomer content in the resulting effluent.

A certain amount of catalyst A was placed in one of the fixed-bed reactors (called bed A), whereas the other one (called bed C), was loaded with a certain amount of commercial crystalline mordenite (catalyst C). The composition of the feed was the same for both reactors. The feed stream was generated by mixing a purified mixture of olefins and paraffins (mixture composition as specified in Example 2) with a suitable amount of dry benzene to obtain the desired benzene to olefin molar ratio. Said starting stream was always kept at a constant flow rate. After this, the stream was divided into two sub-streams through a three-way valve. Each current fed a reactor (after a preheating step), for the purpose of dosing a variable flow to each reactor by controlling the valve (but keeping a constant total flow rate). The effluent emerging from each reactor was mixed, thus generating the final effluent that was analyzed (after separating the benzene and paraffins by means of a distillation process, as was shown in Example 1), by GC-FID. In this Example, both the feed composition and the reaction pressure were kept constant for both reactors, whereas the reaction temperature was different in each reactor and the feed flow rate to each reactor was varied for the purpose of modifying the final 2-phenyl isomer content. The operating conditions are summarized in Table 13.

TABLE 13

| Catalytic bed | A | C |
| --- | --- | --- |
| Particle diameter (mm) | 0.50-1.25 | 0.50-1.25 |
| Catalyst volume (cm$^3$) | 122 | 122 |
| Reaction temperature (° C.) | 100 | 140 |
| Reaction pressure (kg/cm$^2$) | 20 | 20 |
| Reaction LHSV (h$^{-1}$) | 2.7-11.0 | 2.7-11.0 |
| Benzene/olefin molar ratio | 30 | 30 |

It should be taken into account that the liquid hourly space velocity (LHSV) associated to each reactor varies when the initial feed percentage dosed to each reactor varies from 2.7 h$^{-1}$ (when 25% of the initial feed passes through such reactor) to 10.8 h$^{-1}$ (when 100% of the initial feed passes through a single reactor). The product distribution in the final effluent when the feed flows are modified is summarized in Table 14.

TABLE 14

| % of initial feed dosed to each reactor (bed A/bed B) | Total conversion | 2-phenyl isomer content (% by weight) | Heavy alkylate (% by weight) | Branched alkylate (% by weight) |
| --- | --- | --- | --- | --- |
| 100/0 | 99.9 | 18 | 0.9 | 3.8 |
| 75/25 | 99.4 | 30 | 1.1 | 4.4 |
| 50/50 | 99.1 | 43 | 1.3 | 5.1 |
| 25/75 | 98.7 | 55 | 1.4 | 5.7 |
| 0/100 | 98.3 | 70 | 1.6 | 6.3 |

As can be seen in Table 14, the variation of the flow feeding each reactor Implies a variation in the final 2-phenyl isomer content, from 18% by weight (obtained when all the initial feed passes through the bed of catalyst A) to 70% by weight (obtained when all the initial feed goes through the mordenite bed). In all cases, the amount of heavy alkylate detected in the final effluent was less than or equal to 1.6% by weight, and the amount of branched alkylate was always less than 6.5% by weight. Both catalysts show an evident stability against LHSV variations (in terms of conversion and selectivity), in the range of LHSV that was tested.

Example 5

This example shows the advantages of purifying raw alkylbenzene before the sulfonation step, for the purpose of minimizing the sulfonation color of the final sulfonic acid.

A purified mixture of olefins and paraffins, mixed with dry benzene, was used as feed, as described in Examples 2 and 4. A benzene to olefin molar ration of 20:1 was selected. The alkylation was carried out through two parallel isothermal fixed-bed reactors, as in Example 4. The catalysts and operating conditions were exactly the same as in Example 4. For each reactor, a feed dosing of 50% of the initial stream was selected. The raw alkylbenzene was obtained by fractioning the effluent coming from the alkylation step. But the distillation was slightly different when it is compared to the one used in previous examples. In this example, four distillation columns were used. The first column operated at atmospheric pressure, and separated the unreacted benzene at its head, whereas the compounds that were present in the bottom of the column were fed to the second column. The second column, which operated under vacuum, separated the paraffins at its head, whereas the compounds present in the bottom of the column were fed to the third column. The third column, which operated under vacuum, separated the monoalkybenzene at its head, and the heavy alkylate at its bottom. This raw monoalkylbenzene obtained at the head of the third column and containing a certain amount of heavy alkylate, was fed to the adsorption bed. Once the purification was carried out, the adsorption bed effluent was fed to the fourth distillation column. This column separated the light by-products generated during the purification step (mainly benzene, generated through transalkylation reactions at ppm levels) at its head, whereas compounds in the bottom were highly pure mono-alkylbenzenes. These highly pure mono-alkylbenzenes were then sulfonated, using diluted $SO_3$ in dry air as a sulfonating agent, in a multitubular falling film reactor, and then they were matured and hydrolyzed to complete the reaction.

As mentioned before, the purification step was carried out by means of a fixed bed, where a certain amount of commercial acid clay was placed. In this example, a clay was used that was characterized by a weight ratio of silica to alumina of 4.9, partially neutralized with 1.4% by weight of $K_2O$ and 1.2% by weight of MgO, and also characterized by 2.9% by weight of $Fe_2O_3$ and 0.5% by weight of $TiO_2$. This clay was previously activated by passing a hot inert gas stream for the purpose of eliminating the adsorbed water. The activation and operating conditions are summarized in Table 15.

TABLE 15

| Adsorption temperature (° C.) | 110 |
| --- | --- |
| Adsorption LHSV (h$^{-1}$) | 3 |
| Activation temperature (° C.) | 120 |
| Activation LHSV (h$^{-1}$) | 2 |
| Activation period (h) | 12 |
| Activation gas | $N_2$ |

The average sulfonation conditions are summarized in Table 16:

TABLE 16

| $SO_3$/LAB molar ratio | 1.10:1 |
| --- | --- |
| Reaction time | 1.5 hours |
| Reaction temperature | 40-45° C. |
| Digestion time | 1 hour |
| Digestion temperature | 40-45° C. |
| Hydrolysis time | 0.5 hours |
| Hydrolysis temperature | 40-45° C. |

The final sulfonation color was analyzed using a Klett-Summerson colormeter. For the purpose of evaluating the effect of the purification step on the final sulfonation color, the alkylbenzene was also sulfonated under the same conditions, without a purification step. The sulfonation color of the raw sulfonated alkylbenzene and the purified alkylbenzene are summarized in Table 17:

TABLE 17

| Sulfonate | Sulfonation color (Klett-Summerson scale) |
|---|---|
| Raw sulfonated alkylbenzene | 23 |
| Purified sulfonated alkylbenzene | <5 |

As can be seen in Table 17, the purification of the raw alkylbenzene through this selective adsorbent bed implies reducing the final sulfonation color by approximately 80%. When the sulfonation color is reduced, the quality of the neutralized product is increased, especially when it is used in liquid detergent formulations, because it can interfere with the visual effect of the dyes incorporated to the detergent formulation.

Example 6

This example shows the advantages of adding the hydrotropic precursor, obtained when treating the non-linear compounds extracted in the purification step of the alkylation mixture, to the alkylbenzene before its selective adsorption purification step. Both streams were mixed, then purified with an acid clay, and distilled to separate the light by-products and sulfonated, as is described in Example 4, and finally neutralized with aqueous sodium hydroxide in a stoichiometric amount.

Three alkylbenzene samples with different 2-phenyl isomer contents were produced in the alkylation step (as defined in Example 2) for the purpose of evaluating the hydrotropic effect according to the 2-phenyl isomer content. The samples are called S1, S2, and S3, and their 2-phenyl isomer content is summarized in Table 18:

TABLE 18

|  | S1 | S2 | S3 |
|---|---|---|---|
| 2-phenyl alkanes (% by weight) | 18 | 68 | 70 |

The hydrotropic effect of the hydrotropic precursor has been evaluated in terms of the cooling cloud point (CCP) of the final product diluted with water until obtaining typical commercial concentrations. For the purpose of evaluating the effect of the hydrotropic precursor, samples of 90% by weight of the alkylbenzene and 10% of this hydrotropic precursor, were prepared, and then they were diluted with water, Another well-known hydrotrope, sodium xylene sulfonate (SXS), was added to samples with no hydrotropic precursor (90% of pure sodium sulfonate alkylbenzene with variable 2-phenyl isomer content and 10% SXS), and then it was diluted with water to the same concentrations of the previous samples. The results are summarized in Table 19.

TABLE 19

| | Active material in cleaning composition (% by weight in water) | | |
|---|---|---|---|
| | 20% | 25% | 30% |
| | Cooling cloud point (° C.) | | |
| 100% A | 7 | 16 | 25 |
| 90% A + 10% SXS (sodium xylene sulfonate) | 8 | 14 | 20 |
| 90% A + 10% hydrotropic precursor | 1 | 7 | 14 |
| 100% B | 14 | 17 | (*) |
| 90% B + 10% SXS (sodium xylene sulfonate) | 17 | 20 | (*) |
| 90% B + 10% hydrotropic precursor | 13 | 16 | 20 |
| 100% C | 16 | 20 | 24 |
| 90% C + 10% SXS (sodium xylene sulfonate) | 12 | 15 | 17 |
| 90% C + 10% hydrotropic precursor | 7 | 9 | 13 |

(*) Turbid at room temperature

As can be seen in Table 19, the hydrotrope considered in this patent reduces the CCP of the final product in all of the samples, and in all cases its effect is much more stressed than the hydrotropic effect of SXS, being especially interesting when the 2-phenyl isomer content is higher.

Example 7

This example shows the behavior of a zeolite Y doped with 7% by weight of rare earth metals such as La, Ce, Pr and Nd, in the alkylation of benzene with long-chain linear alfa-olefins, in comparison with the results obtained when HF, a catalyst widely used at industrial scale for this same process, is used.

The benzene was dried with a molecular sieve to minimize water addition, and was then mixed with a mixture of long-chain linear alpha-olefins. In the case of the solid catalyst, the pilot plant alkylation tests were carried out in an isothermal fixed-bed reactor, with 24-hour reaction cycles, followed by washing cycles with benzene for the same period. A standard cycle comprises a 24-hour reaction cycle, with a benzene to olefin molar ratio of 50:1, followed by a washing cycle with benzene for the same time period. The operating conditions are summarized in Table 20:

TABLE 20

| Catalyst | A |
|---|---|
| Particle diameter (mm) | 0.50-1.25 |
| Catalyst volume (cm$^3$) | 122 |
| Reaction temperature (° C.) | 140-150 |
| Regeneration temperature (° C.) | 260 |
| Reaction pressure (kgf/cm2) | 20 |
| Regeneration pressure (kgf/cm2) | 40 |
| Reaction LHSV (h$^{-1}$) | 4-8 |
| Regeneration LHSV (h$^{-1}$) | 1 |
| Reaction time (h) | 24 |
| Regeneration time (h) | 24 |
| Benzene/olefin molar ratio | 50 |

The mixture of alpha-olefins used as the feed composition is summarized below in Table 21:

TABLE 21

| Compound | (% by weight) |
|---|---|
| <$C_{20}$-olefin | 0.1 |
| $C_{20}$-olefin | 43.7 |
| $C_{22}$-olefin | 35.3 |
| $C_{24}$-olefin | 19.1 |
| >$C_{40}$-olefin | 0.7 |

Twelve alkylation reaction cycles were carried out using zeolite Y. The first three cycles were carried out with a LHSV of 8 h$^{-1}$, at T=150° C. (cycle A). Then, three cycles were carried out at a LHSV of 6 h$^{-1}$ and T=150° C. (cycle B). The last four cycles were carried out with a LHSV of 4 h$^{-1}$, two of them at T=150° C. and the last two at a lower temperature, T=140° C. (cycle C). All these cycles were carried out for the purpose of analyzing the effect of temperature and space velocity on the yield of the catalyst. The products were analyzed by gas chromatography (GC) and flame ionization detector (FID).

The alkylation with HF was carried out in a refrigerated batch reactor with continuous stirring, given that alkylation is an exothermic reaction and it is necessary to extract heat from the reactor for the purpose of keeping the desired reaction temperature constant, this being characteristic of the state of the art. A certain amount of the previously considered mixture of linear alpha-olefins (composition as shown in Table 20) mixed with dry benzene until the selected benzene to olefin molar ratio was introduced in the reactor. This mixture of benzene and olefins was previously heated until the selected reaction temperature. Then, a certain volume of liquid HF was injected into the reactor until the selected HF to olefin volume ratio. The reaction time was adjusted to 10 minutes, for the purpose of obtaining a LHSV =6 h$^{-1}$, which is typical of the state of the art of the alkylation with HF. The operating conditions of the alkylation reaction with HF are summarized in Table 22:

TABLE 22

| Catalyst | HF |
| --- | --- |
| Reaction temp. (° C.) | 60 |
| Reaction time (min) | 10 |
| HF/olefin volume ratio | 1 |
| Benzene/olefin molar ratio | 10 |

The results gathered in Table 23 correspond to the average product distribution of these cycles using the solid catalyst with different LHSV and temperature conditions (called cycles A, B and C). The results corresponding to HF technology are located in the lower part of Table 23 to compare the yields of HF and the solid catalyst.

TABLE 23

| Cycle | LHSV (h$^{-1}$) | Temperature (° C.) | Conversion | Monolalkyl-benzene (% w) | Light by-products (% w) | Heavy alkylate (% w) | Total by-products % w |
| --- | --- | --- | --- | --- | --- | --- | --- |
| A | 8 | 150 | 99.7 | 99.6 | 0.18 | 0.19 | 0.37 |
| B | 4 | 150 | 99.9 | 99.8 | 0.17 | 0.06 | 0.23 |
| C | 4 | 140 | 99.8 | 99.7 | 0.11 | 0.15 | 0.26 |
| HF | 6 | 60 | 99.9 | 99.7 | 0.20 | 0.10 | 0.30 |

As can be seen in Table 23, the activity of zeolite Y doped with rare earth metals is always above 99.7%, when considered in terms of olefin conversion. This means that zeolite Y exchanged with rare earth metals is highly active. When the generated by-products are analyzed, both catalysts (modified zeolite Y and HF) have a high selectivity with respect to minimizing the light by-products and the heavy alkylate. The amount of total by-products generated by zeolite Y is below 0.4% by weight in the three evaluated cycles, and in cycles B and C it is even lower when HF is used, therefore it is clearly shown that zeolite Y doped with rare earth metals is highly selective in the fixed-bed reactor technology.

The distribution of isomers corresponding to the previous experiments is summarized in Table 24. As in Table 23, the row of results of the lower part corresponds to the results associated with the reaction with HF, with operating conditions as previously defined in Table 22.

TABLE 24

| Cycle | Branched (% w) | 2-phenyl (% w) | 3-phenyl (% w) | 4-phenyl (% w) | 5-phenyl (% w) | 6-phenyl (% w) | 7-phenyl (% w) | 8 and >8-phenyl (% w) |
| --- | --- | --- | --- | --- | --- | --- | --- | --- |
| A | 16.8 | 17.6 | 14.0 | 10.3 | 8.8 | 6.3 | 4.9 | 21.3 |
| B | 18.7 | 17.0 | 13.4 | 10.0 | 8.6 | 6.3 | 4.8 | 21.3 |
| C | 16.4 | 17.7 | 14.4 | 10.4 | 9.0 | 6.3 | 4.7 | 21.4 |
| HF | 12.4 | 19.9 | 12.1 | 8.8 | 8.9 | 7.9 | 6.3 | 23.9 |

In Table 24, the distribution of isomers is relatively similar when the products of zeolite Y are compared with those of HF. The main difference is related to the branched alkylate content. As can be seen, the amount of branched alkylate generated when zeolite Y doped with rare earth metals is used is approximately 4% by weight higher than the amount generated when HF is used as a catalyst. This small difference is not important given that the branched alkylate does not affect the detergent properties. With respect to the 2-phenyl isomer content, it can be seen that HF technology produces a slightly higher amount of 2-phenyl isomer than modified zeolite Y.

Although there are small differences between the product distribution associated to each technology, it has been clearly shown that zeolite Y doped with rare earth metals is able to catalyze the alkylation of benzene with linear $C_{20}$-$_{24}$ alpha-olefins with a high activity in terms of olefin conversion and with a high selectivity for monoalkylbenzenes.

The invention claimed is:
1. A process for obtaining a highly soluble alkyl aromatic sulfonate and with an adjustable 2-phenyl isomer content between 18%-70% by weight, by means of the catalytic alkylation of an aromatic compound with a purified alkylating agent, comprising the following steps:
   i) catalytically dehydrogenating a linear paraffin feed
   ii) selectively hydrogenating the diolefins produced as a by-product in step i) to mono-olefins
   iii) purifying the raw alkylating agent obtained in step ii), separating the non-linear products contained in the effluent of step ii)
   iv) treating the non-linear products extracted in step iii) to form the hydrotropic precursor
   v) alkylating the aromatic hydrocarbon with the mono-olefins present in the purified alkylating agent, by means of the combination of the following alkylation processes
      a) an alkylation process with a catalyst producing a raw linear alkyl aromatic compound with a maximum 2-phenyl isomer content of 20% by weight
      b) an alkylation process with a catalyst producing a raw linear alkyl aromatic compound with a minimum 2-phenyl isomer content of 20% by weight
   vi) fractioning the effluent of step v) for the purpose of separating the aromatic compounds which have not reacted, the paraffins and the heaviest by-products of the linear alkyl aromatic compounds
   vii) purifying the fraction of linear alkyl aromatics coming from step vi)
   viii) sulfonating the purified linear alkyl aromatics obtained in step vii)
   ix) neutralizing the linear alkyl sulfonic acid produced in step viii) wherein the catalyst producing a maximum of 20% by weight of 2-phenyl isomer comprises a FAU type zeolite, between 0.01-0.15% by weight of at least one of the metals selected from the group consisting of: Li, Na, K, Mg or Ca, and between 0.1-8% by weight of at least one of the rare earth metals selected from the group consisting of La, Ce, Pr, Nd, Pm, Sm or Eu; and in that the catalyst producing a minimum of 20% by weight of 2-phenyl isomer comprises a MOR type zeolite, between 0.01%-0.2% by weight of at least one of the metals selected from the group consisting of: Li, Na, K, Mg or Ca, with a maximum of 0.01% of Na, and between 0-0.5% by weight of at least one of the metals selected from the group consisting of Ti, Zr, Hf.

2. A process for obtaining a highly soluble alkyl aromatic sulfonate with an adjustable 2-phenyl isomer content between 18%-70% by weight according to claim 1, wherein the catalyst producing a maximum of 20% of 2-phenyl isomer comprises:
   a) a zeolite with a FAU type isotopic structure
   b) between 0.01-0.15% by weight of at least one of the metals selected from the group consisting of: Li, Na, K, Mg or Ca
   c) between 0.1-8.0% by weight of at least one of the rare earth metals selected from the group consisting of La, Ce, Pr, Nd, Pm, Sm or Eu.

3. A process for obtaining a highly soluble linear alkylbenzene sulfonate with an adjustable 2-phenyl isomer content between 18%-70% by weight according to claim 1, wherein the catalyst producing a maximum of 20% by weight of 2-phenyl isomer comprises:
   a) an X-ray powder diffraction pattern wherein the most intense peak appears at a 2 theta angle corresponding to 6.2°, and the remaining main peaks appear at 2 theta diffraction angles corresponding to 23.6°, 27°, 31.3°, 15.6°, 20.3°, 18.6° and 30°, ordered from greater to lesser intensity of the associated peaks
   b) a total silicon/aluminium molar ratio between 1:1 and 3:1
   c) a total specific area (BET) comprised between 400-700 m$^2$/g
   d) a micropore area comprised between 350-600 m$^2$/g
   e) a specific micropore volume comprised between 0.1-0.3 ml/g
   f) a macropore distribution wherein the macropore diameter is in the range comprised between 20-2000 angstroms.

4. A process for obtaining a highly soluble alkyl aromatic sulfonate with an adjustable 2-phenyl isomer content between 18%-70% by weight according to claim 1, wherein the catalyst producing a minimum of 20% of 2-phenyl isomer comprises:
   a) a zeolite with MOR type isotypic structure
   b) between 0.01%-0.20% by weight of at least one of the metals selected from the group consisting of: Li, Na, K, Mg or Ca
   c) a maximum of 0.01% of Na
   d) between 0-0.5% by weight of at least one of the metals selected from the group consisting of Ti, Zr, Hf.

5. A process for obtaining a highly soluble linear alkylbenzene sulfonate with an adjustable 2-phenyl isomer content between 18%-70% by weight according to claim 1, wherein the catalyst producing a minimum of 20% by weight of 2-phenyl isomer comprises:
   a) an X-ray powder diffraction pattern wherein the most intense peak appears at a 2 theta angle corresponding to 25.6° and the remaining main peaks appear at 2 theta diffraction angles corresponding to 22.3°, 26.3°, 19.6°, 13.5°, and 27.7° ordered from greater to lesser intensity of the associated peaks
   b) a total silicon/aluminium molar ratio between 1.5:1-3.5:1
   c) a total specific area (BET) comprised between 150-600 m$^2$/g
   d) a specific micropore area comprised between 300-450 m$^2$/g
   e) a specific micropore volume comprised between 0.01-0.2 ml/g
   f) a macropore distribution wherein the macropore diameter is in the range comprised between 20-800 angstroms.

6. A process for obtaining a highly soluble linear alkylbenzene sulfonate with an adjustable 2-phenyl isomer content between 18%-70% by weight according to claim 1, wherein the used paraffins comprise between 8-30 carbon atoms.

7. A process for obtaining a highly soluble linear alkylbenzene sulfonate with an adjustable 2-phenyl isomer content between 18%-70% by weight according to claim 1, wherein the aromatic hydrocarbon is selected from the group consisting of: toluene, xylene, benzene or mixtures thereof.

8. A process for obtaining a highly soluble linear alkylbenzene sulfonate with an adjustable 2-phenyl isomer content between 18%-70% by weight according to claim 1, wherein the aromatic hydrocarbon and the purified alkylating agent are mixed before the alkylation reaction of step v) in an aromatic hydrocarbon:olefin molar ratio comprised between 5:1-70:1.

9. A process for obtaining a highly soluble linear alkylbenzene sulfonate with an adjustable 2-phenyl isomer content between 18%-70% by weight according to claim 8, wherein the mixture of the aromatic hydrocarbon and the purified alkylating agent contain a maximum of 0.3% by weight of non-linear compounds other than the aromatic hydrocarbon.

10. A process for obtaining a highly soluble linear alkylbenzene sulfonate with an adjustable 2-phenyl isomer content between 18%-70% by weight according to claim 8, wherein the mixture of the aromatic hydrocarbon and the purified alkylating agent comprises between 0-0.1% by weight of water.

11. A process for obtaining a highly soluble linear alkylbenzene sulfonate with an adjustable 2-phenyl isomer content between 18%-70% by weight according to claim 1, wherein the alkylation reactions of step v) are carried out simultaneously.

12. A process for obtaining a highly soluble linear alkylbenzene sulfonate with an adjustable 2-phenyl isomer content between 18%-70% by weight according to claim 1, wherein the catalyst used in the alkylation reaction is arranged in the reactor in an arrangement selected from the group consisting of: a fixed bed with a single catalyst, a fixed bed with two completely mixed different catalysts, at least two different fixed beds, each one with the same catalyst, at least two different fixed beds, each one with a different catalyst, a slurry reactor with one or more different catalysts.

13. A process for obtaining a highly soluble linear alkylbenzene sulfonate with an adjustable 2-phenyl isomer content between 18%-70% by weight according to claim 1, wherein the alkylation process is carried out in a reactor configuration comprising at least one of the reactor configurations selected from the group consisting of: an independent reactor, at least two parallel reactors, at least two reactors in series and combinations of said configurations.

14. A process for obtaining a highly soluble linear alkylbenzene sulfonate with an adjustable 2-phenyl isomer content between 18%-70% by weight according to claim 1, wherein the purification process is carried out by means of selective adsorption and/or hydrogenation and/or fractioning.

15. A process for obtaining a highly soluble linear alkylbenzene sulfonate with an adjustable 2-phenyl isomer content between 18%-70% by weight according to claim 14, wherein the selective adsorption is carried out by means of a clay type selective adsorbent.

16. A process for obtaining a highly soluble linear alkylbenzene sulfonate with an adjustable 2-phenyl isomer content between 18%-70% by weight according to claim 15, wherein the clay comprises:
   a) a total silica-alumina molar ratio between 3:1-6:1
   b) between 1%-4% by weight of Fe
   c) between 0.5%-2.0% by weight of K, preferably about 1.2% by weight
   d) between 0.2%-2.0% by weight of Mg, preferably about 0.7% by weight
   e) between 0.1-1.0% by weight of $TiO_2$, preferably about 0.3% by weight
   f) a specific area expressed as a BET area comprised between 150-500 $m^2/g$
   g) an accumulative pore volume between 0.1-2 ml/g
   h) a macropore distribution wherein the macropore diameter is comprised between 20-800 angstroms.

17. A process for obtaining a highly soluble linear alkylbenzene sulfonate with an adjustable 2-phenyl isomer content between 18%-70% by weight according to claim 1, wherein the hydrotropic precursor obtained in step iv) is added to the alkyl aromatic compound stream when the 2-phenyl isomer content of the alkyl aromatic compounds is greater than or equal to 60% by weight, being added
   a) just before step vi)
   b) just after step vi).

18. A process for obtaining a highly soluble linear alkylbenzene sulfonate with an adjustable 2-phenyl isomer content between 18%-70% by weight according to claim 1, wherein the hydrotropic precursor obtained in step iv) is individually sulfonated and neutralized and subsequently added to the final alkyl aromatic compound when its 2-phenyl isomer content is greater than or equal to 60% by weight.

19. A process for obtaining a highly soluble linear alkylbenzene sulfonate with an adjustable 2-phenyl isomer content between 18%-70% by weight according to claim 1, wherein the neutralization process of step ix) is carried out by means of an alkaline substance comprising one or more cations selected from the group: Na, K, $NH^{4+}$, Mg, Ca, Ba or substituted ammonium alkalis.

20. A process for obtaining a highly soluble linear alkylbenzene sulfonate with an adjustable 2-phenyl isomer content between 18%-70% by weight according to claim 1, wherein steps i), ii), iii) and iv) are optional.

21. A process for obtaining a highly soluble linear alkylbenzene sulfonate with an adjustable 2-phenyl isomer content between 18%-70% by weight according to claim 20, wherein the olefins of step v) are linear α-olefins.

22. A process for obtaining a highly soluble linear alkylbenzene sulfonate with an adjustable 2-phenyl isomer content between 18%-70% by weight according to claim 20, wherein the olefins of step v) comprise between 9-30 carbon atoms.

23. A process for obtaining a highly soluble linear alkylbenzene sulfonate with an adjustable 2-phenyl isomer content between 18%-70% by weight according to claim 1, wherein the temperature of the reaction is comprised between 20-400° C.

24. A process for obtaining a highly soluble linear alkylbenzene sulfonate with an adjustable 2-phenyl isomer content between 18%-70% by weight according to claim 1, wherein the space velocity is 1-15 $hr^{-1}$.

* * * * *